US011773034B2

(12) United States Patent
Rogers et al.

(10) Patent No.: US 11,773,034 B2
(45) Date of Patent: Oct. 3, 2023

(54) HYPERGOLIC CO-CRYSTAL MATERIAL AND METHOD OF USE THEREOF

(71) Applicant: Acsynam Inc., St-Leonard (CA)

(72) Inventors: Robin Don Rogers, Tuscaloosa, AL (US); Tomislav Friščić, Verdun (CA); Hatem M. Titi, Montreal (CA)

(*) Notice: Subject to any disclaimer, the term of this patent is extended or adjusted under 35 U.S.C. 154(b) by 349 days.

(21) Appl. No.: 16/900,241

(22) Filed: Jun. 12, 2020

(65) Prior Publication Data

US 2020/0392052 A1 Dec. 17, 2020

Related U.S. Application Data

(60) Provisional application No. 62/860,479, filed on Jun. 12, 2019.

(51) Int. Cl.
| | | |
|---|---|---|
| *C06B 47/10* | (2006.01) | |
| *C06B 43/00* | (2006.01) | |
| *C07C 205/06* | (2006.01) | |
| *C07D 241/12* | (2006.01) | |
| *C07D 307/06* | (2006.01) | |
| *C06B 47/02* | (2006.01) | |

(52) U.S. Cl.
CPC .............. *C06B 47/10* (2013.01); *C06B 43/00* (2013.01); *C07C 205/06* (2013.01); *C07D 241/12* (2013.01); *C07D 307/06* (2013.01)

(58) Field of Classification Search
CPC ......... C06B 47/10; C06B 43/00; C06B 47/02; C07C 205/06; C07D 241/12; C07D 307/06
See application file for complete search history.

(56) References Cited

U.S. PATENT DOCUMENTS

| 7,771,549 B1 | 8/2010 | Christe et al. |
| 9,481,840 B2 | 11/2016 | Smith, Jr. et al. |
| 2014/0350266 A1 | 11/2014 | Hages et al. |
| 2014/0373984 A1 | 12/2014 | McCrary et al. |

FOREIGN PATENT DOCUMENTS

| CN | 102992925 B | 11/2014 |

OTHER PUBLICATIONS

Liu et al., 2015, Scientific Reports, 10 pages.*
Vo et al., J. Am. Chem. Soc., 2013, 135, 11757-11790.*
Titi et al., abstract, 2019, caplus an 2019:2114410.*
S. Zhang et al., High-energy metal-organic frameworks (HE-MOFs): Synthesis, structure and energetic performance, Coordination Chemistry Reviews, vol. 307, Part 2, Jan. 15, 2016, pp. 292-312.
V. Thottempudi et al., Tris(triazolo)benzene and Its Derivatives: High-Density Energetic Materials, Angewandte Chemie, vol. 51, Issue 39, Sep. 24, 2012, pp. 9881-9885.
M. B. Talawar et al., Environmentally compatible next generation green energetic materials (GEMs), Journal of Hazardous Materials, vol. 161, Issues 2-3, Jan. 30, 2009, pp. 589-607.
H. M. Titi et al., Hypergolic Triggers as Co-crystal Formers: Co-crystallization for Creating New Hypergolic Materials with Tunable Energy Content, Angewandte Chemie, vol. 58, Issue 51, Dec. 16, 2019, pp. 18399-18404.
Jesus Paulo L. Perez et al., Functionalization and Passivation of Boron Nanoparticles with a Hypergolic Ionic Liquid, Journal of Propulsion and Power, vol. 29, No. 2, Mar. 2013, pp. 489-494.
Giovanni P. Rachiero et al., Versatility and remarkable hypergolicity of exo-6, exo-9 imidazole-substituted nido-decaborane, ChemComm (Chemical Communications), Issue 55, 2017, 53, pp. 7736-7739.
Ajay Kumar Chinnam, Effects of closo-icosahedral periodoborane salts on hypergolic reactions of 70% H2O2 with energetic ionic liquids, Journal of Materials Chemistry A, vol. 6, Issue 41, Nov. 2018, pp. 19997-199989.
Parker D McCrary et al., Nonaborane and Decaborane Cluster Anions Can Enhance the Ignition Delay in Hypergolic Ionic Liquids and Induce Hypergolicity in Molecular Solvents, Inorganic Chemistry, Apr. 9, 2014, 53, pp. 4770-4776.
Qinghua Zhang et al., Energetic Ionic Liquids as Explosives and Propellant Fuels: A New Journey of Ionic Liquid Chemistry, Chemical Reviews, Sep. 10, 2014, 114, 20, pp. 10527-10574 Publication Date:Sep. 10, 2014.
Songqing Li et al., Borohydride Ionic Liquids and Borane/Ionic-Liquid Solutions as Hypergolic Fuels with Superior Low Ignition-Delay Times, Angewandte Chemie, vol. 126, Issue 11, Mar. 10, 2014, pp. 3013-3016.
Stefan Schneider et al., Ionic Liquids as Hypergolic Fuels, Energy & Fuels 2008, 22, 4, pp. 2871-2872 Publication Date: Jun. 17, 2008.
Dr. Onas Bolton et al., Improved Stability and Smart-Material Functionality Realized in an Energetic Cocrystal, Angewandte Chemie, vol. 123, Issue 38, Sep. 12, 2011, pp. 9122-9125.
Kira B. Landenberger et al., Cocrystal Engineering of a Prototype Energetic Material: Supramolecular Chemistry of 2,4,6-Trinitrotoluene, Crystal Growth Design. 2010, vol. 10, 12, pp. 5341-5347, Publication Date: Nov. 2, 2010.
Haixiang Gao et al., Azole-Based Energetic Salts, Chemical Reviews. 2011, 111, 11, pp. 7377-7436, Publication Date:Aug. 12, 2011.
CB Aakeroy et al., Crystal Engineering of Energetic Materials: Co-crystals of Ethylenedinitramine (EDNA) with Modified Performance and Improved Chemical Stability, Chemistry A European Journal, vol. 21, Issue 31, Jul. 27, 2015, pp. 11029-11037.
Naga K. Duggirala et al., Pharmaceutical cocrystals: along the path to improved medicines, ChemComm (Chemical Communications), 2016, 52, pp. 640-655.

(Continued)

*Primary Examiner* — Sun Jae Yoo

(57) ABSTRACT

A hypergolic co-crystal material for producing a hypergol when combined with an oxidizer; it has co-crystals composed at least of a hypergolic trigger component and an energetic coformer.

20 Claims, 6 Drawing Sheets

(56) References Cited

OTHER PUBLICATIONS

S. A. Ross et al., Engineering and manufacturing of pharmaceutical co-crystals: a review of solvent-free manufacturing technologies, ChemComm (Chemical Communications), 2016, 52, pp. 8772-8786.

Andrew V. Trask et al., Pharmaceutical Cocrystallization: Engineering a Remedy for Caffeine Hydration, Crystal Growth & Design 2005, 5, 3, pp. 1013-1021, Publication Date:Feb. 3, 2005.

* cited by examiner

HYPERGOLIC CO-CRYSTAL MATERIAL AND METHOD OF USE THEREOF

The present application claims priority from U.S. provisional patent application No. 62/860,479 filed on Jun. 12, 2019, incorporated by reference herein.

TECHNICAL FIELD

The present disclosure relates to hypergols, and more particularly to hypergolic co-crystals for producing hypergols.

BACKGROUND

Energetic materials, i.e., controllable chemical energy storage systems, are central for a number of civilian applications. Current research in this area is aimed towards materials with specific requirements, such as high energy density, improved thermal stability, low cost, and environmental acceptability. An important class of energetic materials are hypergolic materials, fuels which produce a hypergol or which ignite in contact with an oxidizer, such as white (WFNA) or red fuming nitric acid (RFNA) (for producing e.g. propellants, pyrotechnics and explosives). Hypergolic compounds are ubiquitous in spacecraft and launcher propellant systems, requiring materials with a low ignition delay (ID), defined as the time between ignition and the first contact of the fuel with the oxidizer. The most popular hypergolic components of bipropellant systems today are based on toxic and highly carcinogenic hydrazine and its derivatives, rising concerns of environmental damage. The annual release of cancerogenic hypergolic propellants in the atmosphere was estimated at 12,000 tons globally inspiring the search for safer hypergolic fuels.

Co-crystals are molecular or ionic materials of importance in pharmaceutical materials science, optical materials, fluorescent materials, and have been also been explored as energetic materials. However, the exploration of co-crystals as energetic materials has so far focused on energetic co-crystals, rather than hypergolic co-crystals that can be used as, e.g., hypergolic fuels or a hypergolic trigger/additive.

It would therefore be advantageous to develop a co-crystal that produces a hypergol when combined with an oxidizer, i.e., that ignites when combined with an oxidizer.

SUMMARY

The present disclosure relates to a hypergolic co-crystal that can be used to produce a hypergol when combined with an oxidizer. As such, the hypergolic co-crystal ignites after contact with the oxidizer.

The hypergolic co-crystal can therefore be used as a fuel (a material used to produce heat and/or power) for producing a hypergolic mixture, such as a hypergolic propellant or hypergolic energetic material, or as a hypergolic trigger for ignition of non-hypergolic fuels.

The hypergolic co-crystal has a structure comprising a hypergolic molecular or ionic component, which exhibits hypergolic behavior on its own, combined with at least one other energetic component (a co-crystal former, or a co-former) that may or may not exhibit hypergolic properties on its own.

A broad aspect of the present disclosure is a hypergolic co-crystal material for producing a hypergol when combined with an oxidizer.

In some embodiments, the hypergolic co-crystal material may include a hypergolic trigger component and an energetic coformer.

In some embodiments, the hypergolic trigger component may be selected from: substituted or unsubstituted decaboranes, substituted or unsubstituted silanes, substituted or unsubstituted mercaptanes or a combination thereof.

In some embodiments, the hypergolic trigger component may be selected from decaboranes, and the decaboranes may be substituted decaboranes.

In some embodiments, the substituted decaboranes may include 6-exo,9-exo-bisimidazole decaborane.

In some embodiments, the substituted decaboranes may consist of 6-exo,9-exo-bisimidazole decaborane.

In some embodiments, the energetic coformer may be a nitro-substituted organic compound.

In some embodiments, the energetic coformer may be a nitro-substituted aromatic organic compound.

In some embodiments, the energetic coformer may be a nitrobenzene.

In some embodiments, the energetic coformer may be a nitrogen-containing organic compound.

In some embodiments, the energetic coformer may be a nitrogen-containing aromatic organic compound.

In some embodiments, the energetic coformer may be pyrazine.

In some embodiments, the energetic coformer may be an oxygen-containing organic compound.

In some embodiments, the energetic coformer may be an oxygen-containing aromatic organic compound.

In some embodiments, the energetic coformer may be tetrahydrofuran.

In some embodiments, the hypergolic co-crystal material may exhibit an ignition delay of 50 ms or less when put into contact with the oxidizer, and the oxidizer may be red fuming nitric acid.

In some embodiments, the hypergolic co-crystal material may exhibit an ignition delay of 2 ms or less when put into contact with the oxidizer, and the oxidizer may be white fuming nitric acid.

In some embodiments, the hypergolic trigger component may be selected from a substituted or unsubstituted decaborane, a substituted or unsubstituted silane, a substituted or unsubstituted mercaptane, or a combination thereof, and the energetic conformer may be selected from an aliphatic coformer, an aromatic organic co-former, an inorganic co-former, or a combination thereof.

In some embodiments, the hypergolic trigger component may be selected from a substituted or unsubstituted decaborane, a substituted or unsubstituted silane or a substituted or unsubstituted mercaptane, and the energetic conformer may be selected from an aliphatic coformer, an aromatic organic co-former, an inorganic co-former, or a combination thereof.

In some embodiments, the hypergolic trigger component may be selected from a substituted or unsubstituted decaborane, a substituted or unsubstituted silane or a substituted or unsubstituted mercaptane, and the energetic conformer may be selected from an aliphatic coformer, an aromatic organic co-former or an inorganic co-former.

In some embodiments, the hypergolic trigger component may be a substituted or unsubstituted decaborane.

In some embodiments, the hypergolic trigger component may be ionic and the energetic component may be ionic.

In some embodiments, the hypergolic trigger component may be neutral and the energetic component may be neutral.

Another broad aspect of the present disclosure is the use of the hypergolic co-crystal material, as described in the present disclosure, for producing a hypergol when the hypergolic co-crystal material is combined with an oxidizer, wherein an ignition occurs by combining the hypergolic co-crystal material with the oxidizer.

Another broad aspect of the present disclosure is a hypergol including: the hypergolic co-crystal material, as described in the present disclosure, and an oxidizer, wherein an ignition occurs by combining the hypergolic co-crystal material with the oxidizer.

In some embodiments, the oxidizer may be composed of 70% to 100% by weight of nitric acid.

In some embodiments, the oxidizer may be one of red fuming nitric acid and white fuming nitric acid.

Another broad aspect of the present disclosure is a composition for yielding a hypergol including the hypergolic co-crystal material, as described in the present disclosure, and an oxidizer, wherein an ignition occurs by combining the hypergolic co-crystal material with the oxidizer.

In some embodiments, the oxidizer may be composed of 70% to 100% by weight of nitric acid.

In some embodiments, the oxidizer may be one of red fuming nitric acid and white fuming nitric acid.

Another broad aspect of the present disclosure is a method of producing a hypergol including combining the hypergolic co-crystal material as described in the present disclosure, with an oxidizer, wherein an ignition occurs by combining the hypergolic co-crystal material with the oxidizer.

In some embodiments, the oxidizer may be composed of 70% to 100% by weight of nitric acid.

In some embodiments, the oxidizer may be one of red fuming nitric acid and white fuming nitric acid.

Another broad aspect is a fuel including the hypergolic co-crystal material as described the present disclosure that ignites when combined with an oxidizer.

Another broad aspect is a composition comprising the hypergolic metal organic framework material as defined herein and at least one of an additive and a combustible substance.

In some embodiments, the additive may serve as a catalyst or initiator.

In some embodiments, the additive may include one or more metals.

In some embodiments, the additive may include one or more metals selected from at least one of Ti(0), Al(0), Pd(0) and Zr(0).

In some embodiments, the additive may be an inorganic compound.

In some embodiments, the additive may include one or more inorganic compounds selected from hydrides, azides, cyanamides, nitrates, acetates, sulfates, perchlorates, peroxides, oxides, oximes, oxadiazoles, and picrates.

In some embodiments, the additive may be an inorganic compound selected from ammonium nitrate, ammonium perchlorate and aluminum borohydride.

In some embodiments, the additive may be the oxidizer.

In some embodiments, the hypergolic co-crystal may be present in an amount of 1% to 99% by weight.

In some embodiments, the combustible substance may be present in an amount of 1% to 99% by weight.

In some embodiments, the additive may be present in an amount of 1% to 99% by weight.

In some embodiments, the combustible substance may be a metal or metalloid powder.

In some embodiments, the combustible substance may be a metal or metalloid powder selected from at least one of Al(0), Mg(0), Zn(0), Zr(0), Ti(0), W(0) and Si(0).

In some embodiments, the combustible substance may be an inorganic compound.

In some embodiments, the combustible substance may be an inorganic compound selected from at least one of the groups consisting of boranes, decaborate anions, hydrides, sulfides, hydrazine, hydrazine derivatives, inorganic salts, or peroxides.

In some embodiments, the combustible substance may be an inorganic compound selected from decaborane, hydrazine and aluminum hydride.

In some embodiments, the combustible substance may be an organic compound.

In some embodiments, the combustible substance may be an organic compound with at least one functional group selected from cyano, nitro, amino, alkyl, allyl, alkynyl, butadienyl, phenyl, halides, hydroxyl, carbonyl, peroxy, acetylene, ethylene, oxime, oxadiazole, and vinyl.

In some embodiments, the combustible substance may be an organic compound selected from paraffin, kerosene and nitroglycerin.

In some embodiments, the combustible substance may be a polymeric compound.

In some embodiments, the combustible substance may be an organic polymeric compound selected from one or more groups consisting of polyesters, polysulfides, polyurethanes, resins, nitrates and rubbers.

In some embodiments, the combustible substance may be a polymeric compound selected from hydroxyl terminated polybutadiene, polyethylene, polystyrene and polybutadiene acrylonitrile.

In some embodiments, the additive may be an inorganic compound such as ammonium nitrate, ammonium perchlorate, or aluminum borohydride.

In some embodiments, the additive may be an inorganic compound such as ammonium nitrate, ammonium perchlorate, or aluminum borohydride.

BRIEF DESCRIPTION OF THE DRAWINGS

The invention will be better understood by way of the following detailed description of embodiments of the invention with reference to the appended drawings, in which.

DETAILED DESCRIPTION

Figure 1A:
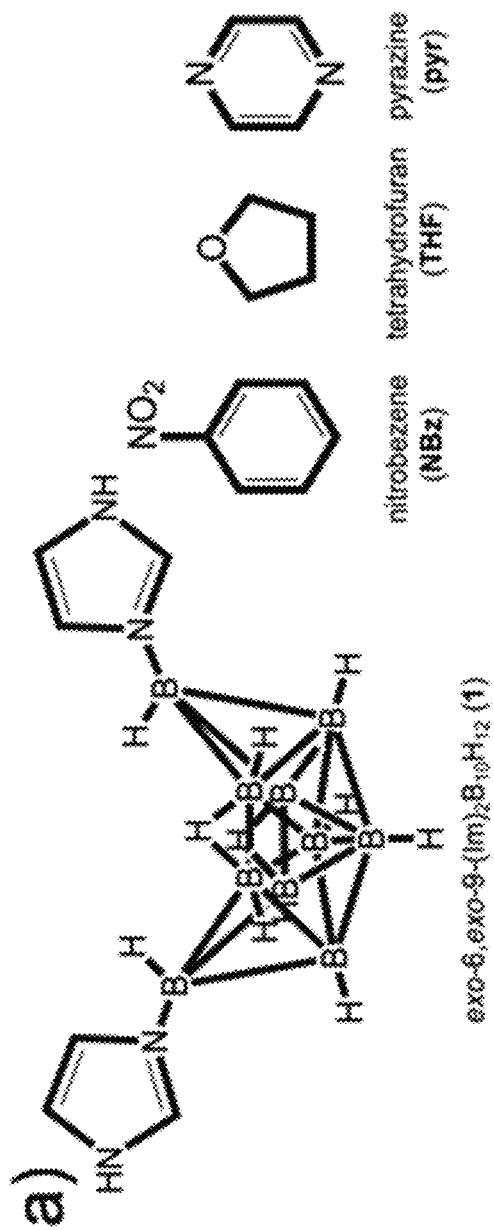
FIG. 1a shows a schematic representation of the 6-exo, 9-exo-bisimidazole decaborane hypergolic co-crystal component.

The present disclosure relates to hypergolic co-crystals which ignite when the hypergolic co-crystal is combined with an oxidizer. The hypergolic reaction is carried out without there needing to be any additives or compounds other than the hypergolic co-crystal and the oxidizer. However, it will be understood that additives may be added to the mixture of the hypergolic co-crystal and the oxidizer without departing from the present teachings.

As such, the hypergolic co-crystals of the present disclosure can be distinguished from energetic co-crystals, where an additional external physical or chemical trigger, aside from the oxidizer, may be required to cause ignition.

Co-crystals include, but are not limited to, materials based on hydrogen bonds, halogen bonds, other types of σ-hole interactions, π . . . π interactions, etc. The co-crystal may be organic, inorganic, and may include one or more organic components, and/or one or more inorganic components.

Co-crystals include, but are not limited to, materials based on neutral molecules, or different combinations of neutral molecules and anion-cation pairs (i.e. salt co-crystals).

The hypergolic co-crystal has a structure where a hypergolic molecule or an ion is found in the same crystal structure with one or more chemically different and energetic molecules or ion pairs that are not necessarily hypergolic on their own.

Preferably, the hypergolic co-crystal has an ignition time equal to or under 10 ms when combined with the oxidizer. In some other embodiments, the hypergolic co-crystal has an ignition time equal or under 4 ms, or equal or under 1 ms, when combined with the oxidizer. For instance, an ignition time equal to or under 10 ms occurs when the hypergolic co-crystal component is 6-exo,9-exo-bisimidazole decaborane, and the other co-crystal component (coformer) is nitrobenzene (however other components may be used in order to achieve an ignition time equal to or under 10 ms).

In some embodiments, the hypergolic component of the hypergolic co-crystal is a borane derivative. Exemplary compound is, but is not limited to, 6-exo,9-exo-bisimidazole decaborane.

In some embodiments, the hypergolic component of the hypergolic co-crystal may have a terminal double bond. In some embodiments, the hypergolic component may have a terminal triple bond.

In some embodiments, the hypergolic component of the hypergolic co-crystal may have a double bond between the first atom of the substituent that is bonded to the aromatic organic linker and the second atom of the substituent that is bonded to the first atom of the substituent.

In some embodiments, the hypergolic component of the hypergolic co-crystal may carry a vinyl group. In some embodiments, it might carry an ethynyl group. However, it could also be any other unsaturated substituent without departing from the present teachings.

In some embodiments, the hypergolic component of the hypergolic co-crystal is a silane derivative.

In some embodiments, the hypergolic component of the hypergolic co-crystal is a mercaptane.

In some embodiments, the energetic coformer in the hypergolic co-crystal may be a nitro-substituted organic compound.

In some embodiments, the energetic coformer in the hypergolic co-crystal may be an oxygen-containing organic compound, such as an ether, ketone, aldehyde, ester, alcohol or a carboxylic acid.

In some embodiments, the energetic coformer in the hypergolic co-crystal may be a heteroatom-containing organic compound, such as ammonia, hydroxylamine or its derivative, hydrazine or its derivative, primary amine, secondary amine, tertiary amine, pyridine, azole or other type of nitrogen-containing heterocycle.

In some embodiments, the energetic coformer may be a heterocyclic ring with one or more N, S and/or O.

The hypergolic co-crystal may be used as a fuel that, when combined with an oxidizer, produces a hypergolic propellant. It will be understood that the hypergolic co-crystal may be for other uses than that of a fuel. It will also be understood that the hypergol resulting from the combination of the hypergolic co-crystal and the oxidizer may be for other uses than that of a hypergolic propellant.

Uses of the hypergolic co-crystal, once combined with an oxidizer, may include, hypergolic propellants, hypergolic energetic materials hypergolic pyrotechnics, etc.

In the present disclosure, by "hypergol", because a hypergol undergoes a reaction once its constituents are combined, it will be understood that it includes, in some examples, the combined constituents (the hypergolic co-crystal and the oxidizer), and in some examples, the separate substituents such that they may be combined at the appropriate time when the use of the hypergol is required.

The constituents of the hypergol may be stored and/or transported in use-appropriate vehicles (e.g. a vehicle or compartment that prevents air exposure).

In some examples, the hypergolic co-crystal may be provided and/or stored in a medium that reduces or eliminates its exposure to external elements (e.g. a liquid medium). The hypergolic co-crystal may be removed from the medium prior to use.

In some embodiments, the method of producing a hypergol results in adding the oxidizer to the hypergolic co-crystal. It will be understood that the conditions of the combining and the environment in which the combining takes place may need to be controlled for safety and/or depending on the use of the hypergol.

Synthesis

Figure 1B:
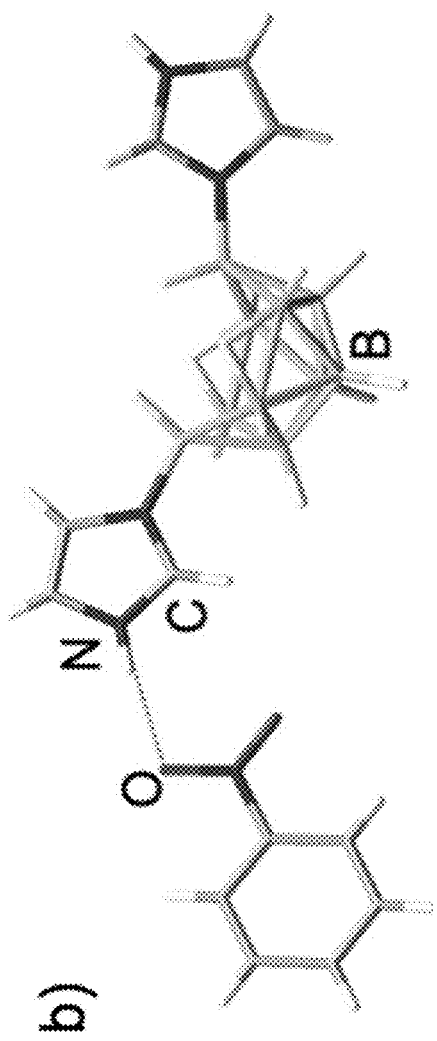
FIG. 1b shows a schematic representation of the co-formers nitrobenzene, pyrazine and tetrahydrofuran.

In a typical synthesis, crystallization of 6-exo,9-exo-bisimidazole decaborane•NBz from acetone containing excess NBz (50 µL) gave red, block-shaped crystals of the hypergolic co-crystal, established by single crystal X-ray diffraction to consist of 6-exo,9-exo-bisimidazole decaborane and NBz molecules connected by N—H . . . O hydrogen bonds (N . . . O length: 2.906(2) Å) between one imidazole moiety of each molecule of 6-exo,9-exo-bisimidazole decaborane and a nitro group of NBz (FIG. 1b).

Definitions

The term "additive" as used herein refers to a substance that either accelerates the reaction, initiates the reaction or enhances the combustion of the reaction. For instance, an additive can be a catalyst or an initiator. Exemplary additives may include hydrides, azides, cyanamides, nitrates, acetates, sulfates, perchlorates, peroxides, oxides and picrates.

The term "co-crystal" refers to a solid crystalline material composed of an active chemical species and one or more co-crystal formers, including but not limited to organic, inorganic, neutral, or ionic chemical species that may or may not be solids at room temperature.

The term a "hypergolic co-crystal" as used herein refers to a co-crystal (e.g. in solid form) that ignites upon contact with an oxidizer and without external aid (such as a spark), composed of one hypergolic component and one energetic coformer.

The term "hypergol" as used herein refers to a substance or composition that ignites without external aid upon contact of its components. For instance, a hypergol may be a hypergolic propellant, a hypergolic explosive, a hypergolic pyrotechnic material, etc.

The term an "oxidizer", "oxidant" or "oxidizing agent" as used herein refers to a substance that is able to oxidize other substances, causing them to lose electrons. Exemplary oxidizers include, but are not limited to, peroxides, nitric acid, nitrate compounds, sulfuric acid, halogen compounds, sodium perborate, hexavalent chromium compounds, peroxydisulfuric acid, peroxymonosulfuric acid, chlorite, chlorate, perchlorate, oxygen, ozone, etc.

The term "combustible substance" as used herein refers to a substance that can be added to a composition including the hypergolic co-crystal that can undergo combustion with the hypergolic co-crystal.

The term "energetic conformer" or "energetic co-crystal former" as used herein refers to an organic molecule or an ion pair that form a chemically, compositionally and structurally-defined crystalline material with the hypergolic co-crystal component to form hypergolic co-crystals. Exemplary coformers include, but are not limited to azoles, nitrobenzenes, pyrazines, ethers, etc.

The term "hypergolic trigger component" as used herein refers to a component of the co-crystal that is hypergolic, and may be an organic, inorganic molecule or ion that forms an ion pair with a corresponding energetic coformer.

Exemplary Study:

The following study provides non-limitative examples of hypergolic co-crystals of the present disclosure.

Co-crystal formation is a powerful technique of crystal engineering that uses the formation of solid-state molecular complexes held by non-covalent forces, such as hydrogen or halogen bonds, as a means to generate crystalline solids with new or improved properties. Co-crystallization has been used with particular success in context of pharmaceutical materials[1] and to modify solid-state properties of energetic molecules,[2] leading to explosives with tailored properties, including oxygen balance, density, heat of formation, sensitivity (to electrostatic discharge, friction, impact), stability, etc.[3]

The first use of co-crystallization to generate and tune hypergolic solids,[4,5] i.e. a material capable of spontaneous ignition and combustion upon contact with external oxidizer, by combining a hypergolic trigger with an energy rich, non-hypergolic molecule, is herein demonstrated. A critical property for a hypergol is the ignition delay (ID): the time between contact with an oxidizer and ignition, required to be 50 ms or less.[6] While hypergols are necessary components of propulsion systems in rockets and spacecraft, the currently used systems rely on highly toxic and carcinogenic hydrazine propellants, inspiring a search for greener, safer alternatives.[7,8] Decaborane (n-$B_{10}H_{14}$) derivatives were shown to be particularly promising in the design of hypergolic ionic liquids, combining low sensitivity and vapor pressure with low ID. Just like other hypergolic compounds, the energy content of a decaborane is based on its covalent structure, specifically the energy-rich B—B and B—H bonds.[9,10] Consequently, modification of the energy content of a solid hypergol requires either covalent modification or blending, both of which will affect its ID.[11]

In contrast, it is now shown that a design for hypergolic solids whose energy content can be fine-tuned by supramolecular chemistry can be achieved, without changes to the covalent structure of the hypergol or its ID. Central to this proof-of-principle study is the 6-exo,9-exo-bisimidazole decaborane (1, FIG. 1a), previously shown to be hypergolic.[12] The decaborane unit of 1 is flanked by nitrogen-rich imidazole moieties with N—H groups which should enable it to act as a hydrogen bond donor in co-crystallization. By using nitrobenzene (NBz)[13] as a model energetic, but non-hypergolic hydrogen bond acceptor, the first example of a new hypergolic material obtained by co-crystallization is demonstrated. Whereas NBz is not hypergolic, the co-crystal 1•NBz exhibits an ultrashort ID on par with hypergolic 1, but (FIGS. 1d,e) with a modified energy density (Table 1).

Figure 1C:
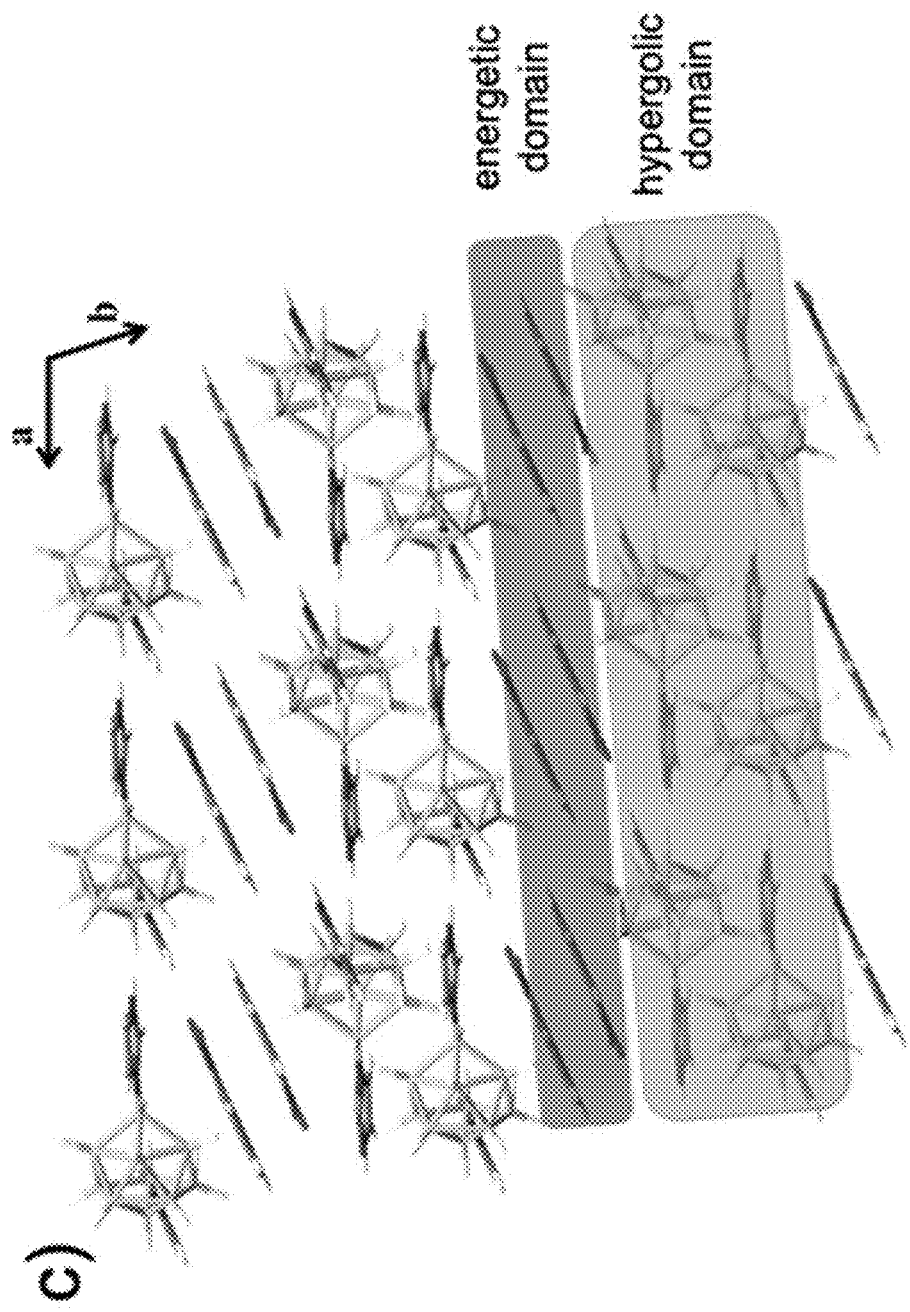
FIG. 1c shows a schematic representation of Hypergolic (6-exo,9-exo-bisimidazole decaborane) and energetic (nitrobenzene) domains in the crystal structure of the hypergolic co-crystal with the nitrobenzene co-crystal former.
Figures 1D, 1E:
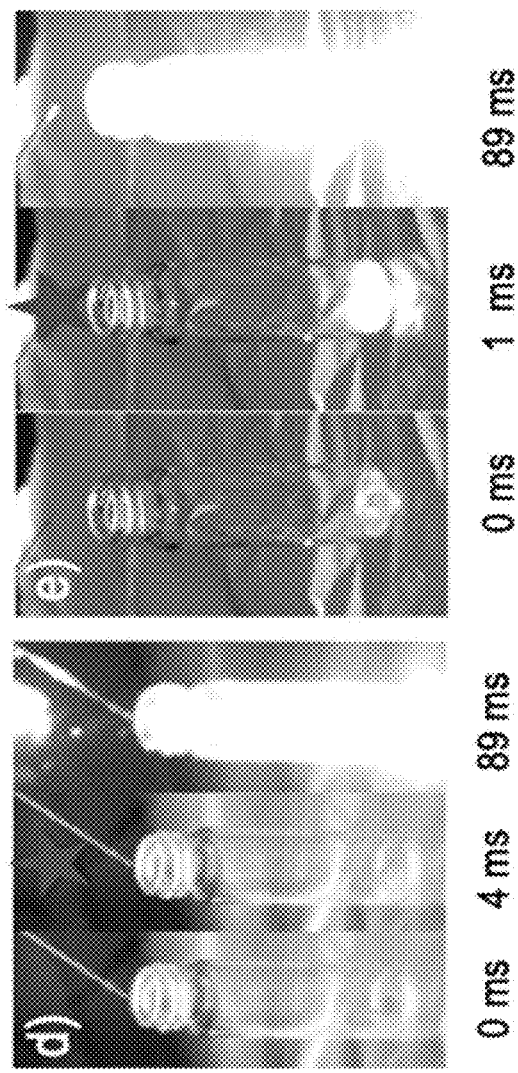
FIG. 1d shows a set of selected photographs for a hypergolicity drop test for the 6-exo,9-exo-bisimidazole decaborane hypergolic co-crystal with nitrobenzene, with each test done in triplicate.
FIG. 1e shows a set of selected photographs for the hypergolicity drop testing of pure solid 6-exo,9-exo-bisimidazole decaborane, with each test done in triplicate.

Crystallization of 1 (5 mg) from acetone containing excess NBz (50 µL) gave red, block-shaped crystals of 1•NBz, established by single crystal X-ray diffraction to consist of 1 and NBz molecules connected by N—H . . . O hydrogen bonds (N . . . O length: 2.906(2) Å) between one imidazole moiety of each molecule of 1 and a nitro group of NBz (FIG. 1b). The second imidazole group on each molecule of 1 is involved in short H . . . H interactions on one of the triangular faces of a neighboring decaborane unit. These hydrogen-bonding motifs give rise to supramolecular chains of 1 decorated by NBz molecules. This structure, which represents the so far first reported hypergolic co-crystal of a decaborane unit, can be analyzed in terms of a separate hypergolic domain, consisting of molecules of 1, and energetic domain containing NBz molecules, held together through N—H . . . O hydrogen bonds (FIG. 1c).

The ID for 1•NBz was measured using the standard drop tests using white fuming nitric acid (WFNA) as the oxidizer. In each test, a single drop (10 µL) of WFNA was released from a fixed height (5 cm) using a 100 µL Hamilton syringe into a vial containing ca. 3 mg of the solid co-crystal. The hypergolic test was monitored using a Redlake MotionPro Y4 high speed camera, recording at 1,000 frames/s. Each drop test was performed in triplicate. The drop tests on 1•NBz reveal an ultrashort ID of 4(1) ms (FIG. 1d) and intense green-red flames of ca. 4 cm height, lasting ca. 250 ms. While the ID of 1•NBz is similar to the 2(1) ms delay for 1 (FIG. 1$e^{12}$), the observed flame was more vigorous and lasted ca. twice as long compared to 1. The improvement in combustion intensity can be explained both by the presence of NBz in the co-crystal, which provides additional energy for combustion, as well as increased density of 1•NBz compared to 1: at 100 K, the calculated densities of 1•NBz and 1 are 1.238 g cm$^{-3}$ and 1.197 g cm$^{-3}$, respectively,[11,12] revealing an almost 3.5% density increase upon co-crystallization. Consequently, 1•NBz demonstrates the ability to modify the combustion properties, as well as density of a known hypergolic building block.

It was also evaluated whether 1•NBz could be used as a hypergolic trigger for ignition of the energetic but non-hypergolic liquid NBz. Drop tests on co-crystals moist with liquid NBz revealed a slightly increased ID of 8(2) ms, probably due to slower diffusion of the oxidant to the hypergol due to a coating of NBz on the co-crystal, but with more intense green-red flames (see SI). Nevertheless, this confirms that hypergolic activity of 1•NBz is sufficient for the ignition of a small excess of a non-hypergolic fuel. In contrast, no ignition was observed in drop tests on solid 1 (3 mg) suspended by sonication in NBz (90 µL), consistent with the higher energy output of the co-crystal.

Increased reactivity of energetic materials and hypergols was previously associated with a reduction in bandgap.[14] Indeed, solid-state UV/Vis spectroscopy measurements on 1•NBz reveal a small bandgap of 1.83 eV, which is consistent with its hypergolicity and red color, and is also lower than the measured bandgap for 1 (3.40 eV), which is also consistent with its colourless appearance.[15] Lowering of the bandgap upon co-crystallization is explained by density of states (DOS) calculations (see SI) which reveal that the highest occupied crystal orbital (HOCO) band of 1•NBz is entirely localized on the NBz molecules. Since the HOMO of NBz is higher in energy than the HOMO of 1, introducing NBz into the crystal structure effectively reduces the bandgap.[16]

Stability of 1•NBz was evaluated by theoretical and experimental methods. Theoretical calculations were performed using CRYSTAL17 periodic density functional theory (DFT), with crystal structures of 1 (CSD[18] code PECTUP[12]), NBz (CSD code UHATUS[19]) and 1•NBz geometry-optimized, and their energies used to calculate the enthalpy of formation (see SI for details). Calculations show that the enthalpy of formation of 1•NBz from individual components is slightly endothermic, +0.04 kJ mol$^{-1}$, and co-crystal formation is most likely entropy-driven. However, as the calculations assumed both starting materials are in crystalline form (NBz melts at 5.7° C.) the co-crystal formation at room temperature is expected to be more exothermic.

Thermogravimetric analysis (TGA) reveals that 1•NBz undergoes a weight loss step at Tonset of 59° C., while differential scanning calorimetry (DSC, FIG. 2a) from −90° C. to 80° C. revealed an endothermic event with an onset of 62° C. consistent with the TGA observation. During repeated heating and cooling cycles, the sample exhibited an exothermic event at ca. −16° C. during cooling, and an endothermic event at ca. 4° C. during heating. These observations are consistent with 1•NBz separating into 1 and NBz around 60° C., with the exo- and endothermic events upon repeated cooling and heating corresponding to crystallization and melting of NBz.

Figure 2:
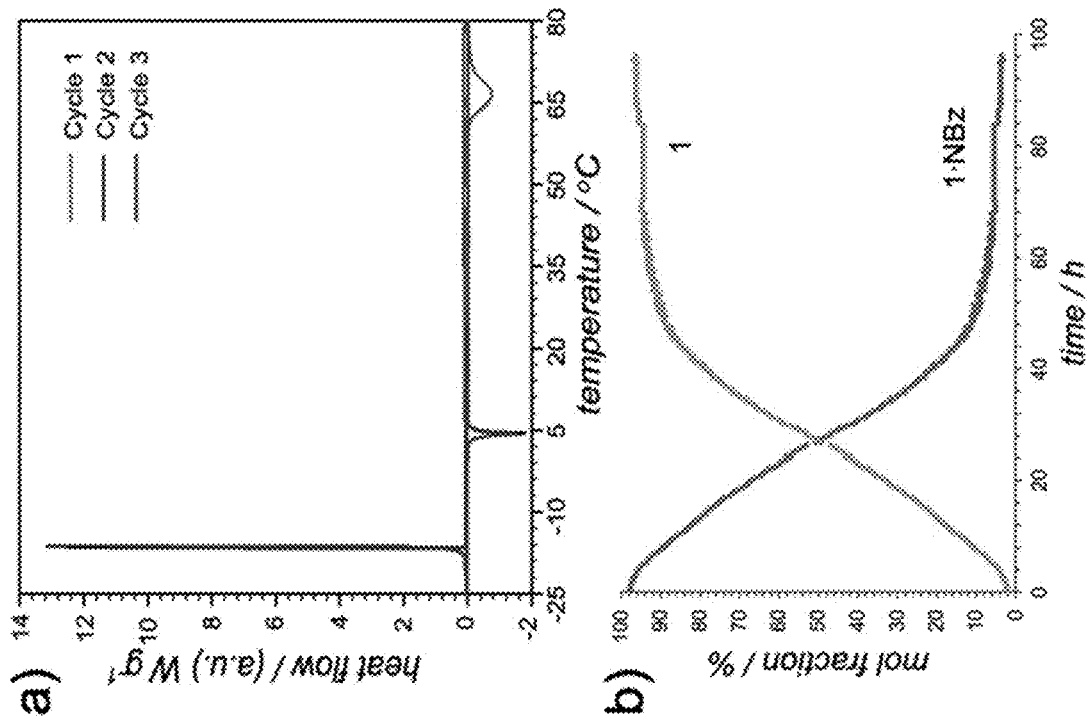
FIG. 2 shows (a) the DSC thermogram of the 6-exo,9-exo-bisimidazole decaborane hypergolic co-crystal with nitrobenzene, in the temperature range from −25° C. to 80° C. (b) Time-dependent loss of nitrobenzene from the 6-exo, 9-exo-bisimidazole decaborane hypergolic co-crystal with nitrobenzene upon standing in open air, based on Rietveld analysis of powder X-ray diffraction data.

The stability of 1•NBz below 60° C. was verified by repeatedly heating a sample from −90° C. to 35° C., holding for 10 minutes at 35° C., and then cooling again to −90° C. (FIG. S2). There was no change in DSC thermogram upon three such cycles, confirming that 1•NBz is stable in a confined environment up to at least 35° C. The co-crystal was stable upon storage in a closed vial for at least a month, but in open air slowly released NBz to form 1. Monitoring by X-ray powder diffraction (FIG. S5) and Rietveld analysis using TOPAS Academic v. 6 (Coelho Software) revealed that 50% of 1•NBz transforms to crystalline 1 upon sitting in open air for ca. 30 hours (FIG. 2b).

Figure 3:
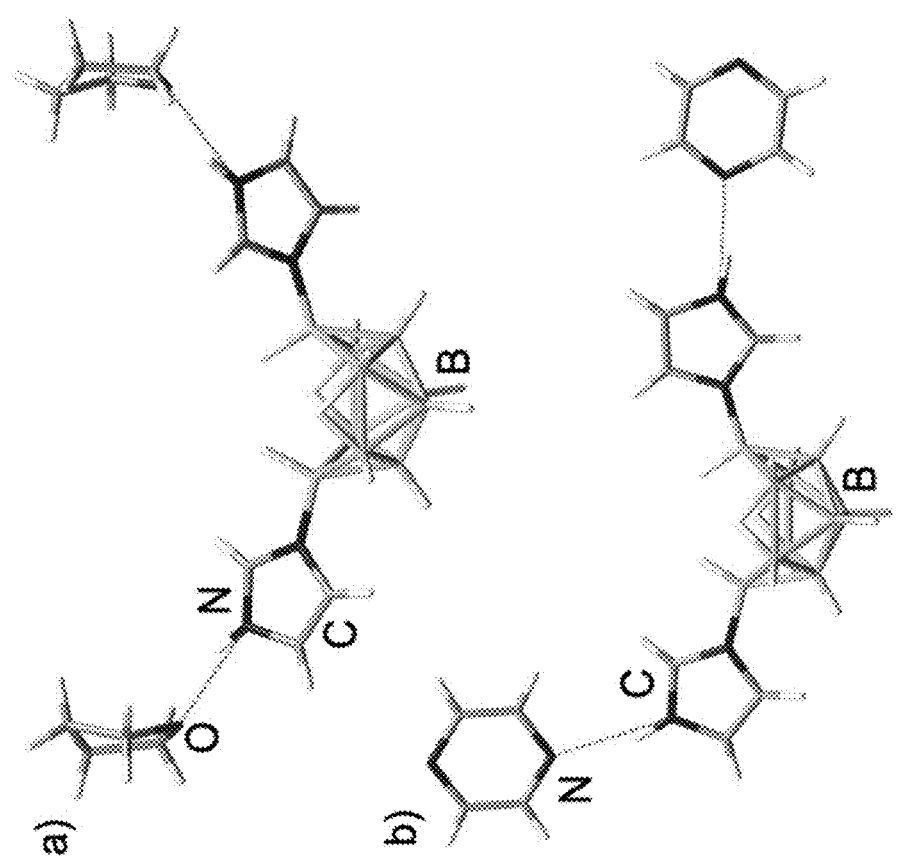
FIG. 3 (a) shows a fragment of the 6-exo,9-exo-bisimidazole decaborane hypergolic co-crystal with tetrahydrofuran, highlighting the interaction between the 6-exo,9-exo-bisimidazole decaborane hypergolic component and tetrahydrofurane co-crystal former; and (b) shows a fragment of the 6-exo,9-exo-bisimidazole decaborane hypergolic co-crystal with pyrazine, highlighting the interaction between the 6-exo,9-exo-bisimidazole decaborane hypergolic component and pyrazine co-crystal former.

The ability of 1 to form co-crystals is not limited only to NBz. Screening for different hydrogen bond acceptors has so far revealed co-crystals with tetrahydrofuran (THF) as well as pyrazine (pyr), demonstrating the ability to form co-crystals with aliphatic molecules and with solids, respectively. The co-crystal 1•2THF was obtained by slow evaporation from a solution of 1 (1 mmol) in a mixture of THF and benzene (50:50 v/v, 5 mL), in the form of colorless crystals. Single crystal X-ray diffraction revealed a structure of tetragonal space group P4$_1$2$_1$2, with asymmetric unit containing one molecule of THF and a one half-molecule of 1 situated on a two-fold rotation axis (FIG. 3a). Both imidazole groups of 1 are involved in N—H . . . O hydrogen bonds with neighboring molecules of THF (N . . . O separation 2.722(2) Å), forming discrete 1•2THF assemblies that further interact through H(δ−) . . . H(δ+) and π-stacking interactions to form one dimensional non-covalent chains.

Co-crystallization of 1 with pyr as a solid co-crystal former was first explored by milling of the two materials in a 1:1 stoichiometric ratio, producing only a poorly crystalline material, characterized by PXRD. However, re-crystallization of the milled material from acetone followed by slow evaporation produced a small number of orange plate-shaped crystals of 1•pyr. In contrast to both 1•NBz and 1•2THF, the co-crystal 1•pyr is composed of extended, zigzag-shaped chains of alternating molecules of pyr and 1 held by N—H . . . N hydrogen bonds (N . . . N distances 2.932(6) Å and 2.947(6) Å, FIG. 3b. Preliminary investigation of hypergolic properties of 1•pyr indicates an ID of 1 ms, with an approximate height of 4.5 cm of red-green flames (see SI), confirming the ability to use co-crystal formation as a way to generate hypergolic materials.

Combustion energies of co-crystals in comparison to 1 were investigated through CRYSTAL14 periodic DFT calculations, using a hybrid B3LYP20 functional combined with a Grimme D3 dispersion correction.21 The wave function was described with a pob-TZVP basis set, specifically adapted for periodic calculations,[22] and the first Brillouin zone was sampled with a 0.03 Å-1 k-point grid density. Besides the crystalline materials, gas-phase DFT energies were calculated for $O_2$, $CO_2$, $H_2O$ and $N_2$ molecules (see SI). Combustion energies were calculated following the equations:

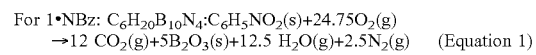

For 1•NBz: $C_6H_{20}B_{10}N_4$:$C_6H_5NO_2$(s)+24.75$O_2$(g)
→12 $CO_2$(g)+5$B_2O_3$(s)+12.5 $H_2O$(g)+2.5$N_2$(g)     (Equation 1)

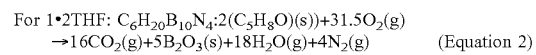

For 1•2THF: $C_6H_{20}B_{10}N_4$:2($C_5H_8O$)(s))+31.5$O_2$(g)
→16$CO_2$(g)+5$B_2O_3$(s)+18$H_2O$(g)+4$N_2$(g)     (Equation 2)

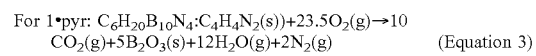

For 1•pyr: $C_6H_{20}B_{10}N_4$:$C_4H_4N_2$(s))+23.5$O_2$(g)→10 $CO_2$(g)+5$B_2O_3$(s)+12$H_2O$(g)+2$N_2$(g)     (Equation 3)

Calculated combustion enthalpies of the co-crystals are all higher than for 1, which is consistent with the presence of additional fuel components in each co-crystal and with the observed enhancement in combustion properties of 1•NBz compared to 1. Importantly, the energetic properties of the co-crystals remain significantly higher than for conventional energetic materials, such as trinitrotoluene (TNT, Table 1, Entry 5).

TABLE 1

Calculated combustion properties for 1 and corresponding co-crystals.

| Material | Combustion enthalpy/ kJ mol$^{-1}$ | Gravimetric energy density/ kJ g$^{-1}$ | Volumetric energy density/ kJ cm$^{-3}$ |
| --- | --- | --- | --- |
| 1 | −11815 | 46.10 | 55.16 |
| 1•NBz | −14993 | 39.52 | 48.92 |
| 1•2THF | −16824 | 42.00 | 46.92 |
| 1•pyr | −14077 | 41.84 | 51.82 |
| TNT | −3494 | 15.38 | 26.22 |

In summary, it has been demonstrated that co-crystallization of a hypergolic trigger molecule with an energetic or hypergolic component, enables the energy output as well as density of a hypergolic solid to be varied without affecting its ignition delay. This enables a simple strategy to generate new hypergolic materials by combining hypergolic and fuel components through supramolecular chemistry, herein illustrated by using a highly hypergolic building block based on a decaborane unit substituted with imidazole groups suitable for hydrogen bonding. Co-crystallization of this hypergolic building block with nitrobenzene as the fuel component yields a co-crystal with a higher density and significantly improved combustion properties compared to the starting material, but with the retention of ultrashort ID. It is evident that this strategy should be of high value in the development of new hypergolic fuels, as it is simple and avoids the use of covalent chemistry to generate new materials, free of hazardous hydrazine components, with high energy of combustion and extremely short ignition delay.

1. a) A. V. Trask, W. D. S. Motherwell, W. Jones, Cryst Growth Des. 2005, 5, 1013-1021; b) S. A. Ross, D. A. Lamprou, D. Douroumis, Chem. Commun., 2016, 52, 8772-8786; c) N. K. Duggirala, M. L. Perry, Ö. Almarsson, M. J. Zaworotko, Chem. Commun. 2016, 52, 640-655.
2. a) C. B. Aakeröy, T. K. Wijethunga, J. Desper. Chem. Eur. J. 2015, 21, 11029-11037; b) H. Gao, J. M. Shreeve, Chem. Rev. 2011, 111, 7377-7436; c) K. Landenberger, A. Matzger, Cryst. Growth Des., 2010, 10, 5341-5347.
3. a) O. Bolton, A. J. Matzger. Angew. Chem. Int. Ed. 2011, 50, 8960-8963; b) T. Brinck, Green energetic materials, John Wiley & Sons, Ltd., Chichester, UK, 2014; c) J. J. Sabatini, K. D. Oyler, Crystals 2015, 6, 5-22; d) D. Trache, T. M. Klapötke, L. Maiz, M. Abd-Elghany, L. T. DeLuca, Green. Chem. 2017, 19, 4711-4736; e) Y. Xu, Q. Wang, C. Shen, Q. Lin, P. Wang, M. Lu, Nature 2017, 549, 78-82.
4. Y. Zhang, H. Gao, Y.-H. Joo, J. M. Shreeve, Angew. Chem. Int. Ed. 2011, 50, 9554-9562.
5. S. Schneider, T. Hawkins, M. Rosander, G. Vaghjiani, S. Chambreau, and G. Drake, Energy Fuels 2008, 22, 2871-2872.
6. S. Li, H. Gao, J. M. Shreeve, Angew. Chem. Int. Ed. 2014, 53, 2969-2972.
7. a) Q. Zhang, J. M. Shreeve, Chem. Rev. 2014, 114, 10527-10574; b) H. Tan, H. Terashima, M. Koshi, Y. Daimon, Proceedings of the Combustion Institute 2015, 35, 2199-2206; c) L. T. De Luca, T. Shimada, V. P. Sinditskii, M. Calabro, eds., Chemical rocket propulsion: A comprehensive survey of energetic materials, Springer, 2016.
8. a) M. B. Talawar, R. Sivabalan, T. Mukundan, H. Muthurajan, A. K. Sikder, B. R. Gandhe, A. S. Rao, J. Hazard. Mater. 2009, 161, 589-607; b) V. Thottempudi, F. Forohor, D. A. Parrish, J. M. Shreeve, Angew. Chem. Int. Ed. 2012, 51, 9881-9885; c) S. Zhang, Q. Yang, X. Liu, X. Qu, Q. Wei, G. Xie, S. Chen, S. Gao, Coord. Chem. Rev. 2016, 307, 292-312.
9. P. D. McCrary, P. S. Barber, S. P. Kelley, R. D. Rogers, Inorg. Chem. 2014, 53, 4770-4776
10. J. G. Speight, Lange's handbook of chemistry. Vol. 1. New York: McGraw-Hill, 2005.
11. a) A. A. Fiorillo, J. M. Galbraith, J. Phys. Chem. A, 2004, 108, 5126-5130; b) M. V. K. Bhosale, S. G. Kulkarni, P. S. Kulkarni, ChemistrySelect 2016, 1, 1921-1925; c) A. K. Chinnam, N. Petrutik, K. Wang, A. Shlomovich, O. Shamis, D. S. Tov, M. Sućeska, Q. L. Yan, R. Dobrovetsky, M. Gozin, Journal of Materials Chemistry A, 2018, 6, 19989-19997; d) B. V. S. Jyoti, M. S. Naseem, S. W. Baek, Combustion and Flame 2017, 176, 318-325; e) H. M. Titi, J. M. Marrett, G. Dayaker, M. Arhangelskis, C. Mottillo, A. J. Morris, G. P. Rachiero, T. Friščić, R. D. Rogers, Sci. Adv. 2019, 5, eaav9044
12. G. P. Rachiero, H. M. Titi, R. D. Rogers, Chem. Commun. 2017, 53, 7736-7739.
13. H. Schubert, A. Kuznetsov, Detection of liquid explosives and flammable agents in connection with terrorism. Springer Science & Business Media; 2008.
14. R. Dovesi, A. Erba, R. Orlando, C. M. Zicovich-Wilson, B. Civalleri, L. Maschio, M. Rérat, S. Casassa, J. Baima, S. Salustro, B. Kirtman, Wiley Interdiscip. Rev. Comput. Mol. Sci. 2018, 8, e1360.
15. C. R. Groom, I. J. Bruno, M. P. Lightfoot, S. C. Ward, Acta Crystallogr., Sect. B: Struct. Sci., Cryst. Eng. Mater., 2016, 72, 171-179.
16. D. Stasko, S. P. Hoffmann, K.-C. Kim, N. L. P. Fackler, A. S. Larsen, T. Drovetskaya, F. S. Tham, C. A. Reed, C. E. F. Rickard, P. D. W. Boyd, E. S. Stoyanov, J. Am. Chem. Soc. 2002, 124, 13869-13876.
17. a) A. D. Becke, J. Chem. Phys. 1993, 98, 5648-5652; b) P. J. Stephens, F. J. Devlin, C. F. Chabalowski, M. J. Frisch, J. Phys. Chem. 1994, 98, 11623-11627.
18. S. Grimme, J. Antony, S. Ehrlich, H. Krieg, J. Chem. Phys. 2010, 132, 154104.
19. M. F. Peintinger, D. Vilela Oliveira, T. Bredow, J. Comput. Chem. 2013, 34, 451-459.
20. a) W. Zhu, H. Xiao, Struct. Chem. 2010, 21, 657-665; b) Z. Zheng, X. Jiang, J. Zhao, Chem. Phys. Lett. 2015, 628, 76-80.
21. J. Tauc, R. Grigorovici, A. Vancu, Phys. Status Solidi 1966, 15, 627-637.
22. M. Arhangelskis, M. D. Eddleston, D. G. Reid, G. M. Day, D.-K. Bučar, A. J. Morris, W. Jones, Chem. Eur. J. 2016, 22, 10065-10073.

What is claimed is:

1. A hypergolic co-crystal material for producing a hypergol when combined with an oxidizer.

2. The hypergolic co-crystal material as defined in claim 1, wherein the composition of the hypergolic co-crystal material comprises a hypergolic trigger component and an energetic coformer.

3. The hypergolic co-crystal material as defined in claim 2, wherein the hypergolic trigger component is selected from: substituted or unsubstituted decaboranes, substituted or unsubstituted silanes, substituted or unsubstituted mercaptanes, and a combination thereof.

4. The hypergolic co-crystal material as defined in claim 3, wherein the hypergolic trigger component is selected from decaboranes, and wherein the decaboranes are substituted decaboranes.

5. The hypergolic co-crystal material as defined in claim 4, wherein the substituted decaboranes comprise 6-exo,9-exo-bisimidazole decaborane.

6. The hypergolic co-crystal material as defined in claim 2, wherein the energetic coformer is a nitro-substituted aromatic organic compound.

7. The hypergolic co-crystal material as defined in claim 2, wherein the energetic coformer is a nitrobenzene.

8. The hypergolic co-crystal material as defined in claim 2, wherein the energetic coformer is a nitrogen-containing aromatic organic compound.

9. The hypergolic co-crystal material as defined in claim 2, wherein the energetic coformer is pyrazine.

10. The hypergolic co-crystal material as defined in claim 2, wherein the energetic coformer is an oxygen-containing aromatic organic compound.

11. The hypergolic co-crystal material as defined in claim 2, wherein the energetic coformer is tetrahydrofuran.

12. The hypergolic co-crystal material as defined in claim 2, wherein the hypergolic trigger component is selected from a substituted or unsubstituted decaborane, a substituted or unsubstituted silane or a substituted or unsubstituted mercaptane, and wherein the energetic conformer is selected from an aliphatic coformer, an aromatic organic co-former, an inorganic co-former, or a combination thereof.

13. The hypergolic co-crystal material as defined in claim 12, wherein the hypergolic trigger component is a substituted or unsubstituted decaborane.

14. The hypergolic co-crystal material as defined in claim 2, wherein the hypergolic trigger component is ionic and the energetic component is ionic.

15. The hypergolic co-crystal material as defined in claim 2, wherein the hypergolic trigger component is neutral and the energetic component is neutral.

16. A composition comprising the hypergolic metal organic framework material as defined in claim 2 and at least one of an additive and a combustible substance.

17. A composition for yielding a hypergol comprising:
the hypergolic co-crystal material as defined in claim 1; and
an oxidizer,
wherein an ignition occurs by combining the hypergolic co-crystal material with the oxidizer.

18. The composition as defined in claim 17, wherein the oxidizer is composed of 70% to 100% by weight of nitric acid.

19. The composition as defined in claim 17, wherein the oxidizer is one of red fuming nitric acid and white fuming nitric acid.

20. A method of producing a hypergol comprising:
combining the hypergolic co-crystal material as defined in claim 1 with an oxidizer, wherein an ignition occurs by combining the hypergolic co-crystal material with the oxidizer.

* * * * *